United States Patent [19]

Lukacsko et al.

[11] Patent Number: 5,071,842

[45] Date of Patent: Dec. 10, 1991

[54] ASPIRIN-CONTAINING COMPOSITION INCLUDING DIPHENHYDRAMINE AND AN ALKALIZING AGENT TO REDUCE GASTROINTESTINAL INJURY POTENTIAL

[75] Inventors: Alison B. Lukacsko, Robbinsville; Joseph J. Piala, Metuchen, both of N.J.

[73] Assignee: Bristol-Myers Squibb Company, New York, N.Y.

[21] Appl. No.: 456,062

[22] Filed: Dec. 21, 1989

Related U.S. Application Data

[63] Continuation of Ser. No. 259,480, Oct. 14, 1988, abandoned, which is a continuation of Ser. No. 887,673, Jul. 18, 1986, abandoned.

[51] Int. Cl.$^5$ ............... A01N 43/00; A01N 31/62; A01N 37/36
[52] U.S. Cl. ................... 514/161; 514/162; 514/165
[58] Field of Search ............... 514/159, 161, 162

[56] References Cited

U.S. PATENT DOCUMENTS

| 4,401,665 | 8/1983 | Sheinaus et al. | 514/162 |
| 4,522,826 | 6/1985 | Sunshine et al. | 514/569 |
| 4,664,915 | 5/1986 | Simonian | 424/128 |

FOREIGN PATENT DOCUMENTS

| 0248150 | 12/1987 | European Pat. Off. . |
| 2082456 | 3/1982 | United Kingdom . |
| 2105193 | 3/1983 | United Kingdom . |

*Primary Examiner*—Jerome D. Goldberg
*Assistant Examiner*—T. J. Criares
*Attorney, Agent, or Firm*—Charles J. Zeller

[57] ABSTRACT

A nonsteroidal anti-inflammatory drug composition containing as protectants against gastrointestinal injury, $H_1$ blockers, $H_2$ blockers, beta-adrenergic agonists, or combination thereof, and an alkalizing agent and a process for administering such compositions.

2 Claims, No Drawings

ASPIRIN-CONTAINING COMPOSITION INCLUDING DIPHENHYDRAMINE AND AN ALKALIZING AGENT TO REDUCE GASTROINTESTINAL INJURY POTENTIAL

This is a continuing application of application Ser. No. 259,480 filed Oct. 14, 1989, now abandoned, which is a continuing application of application Ser. No. 887,673 filed July 18, 1986, now abandoned.

This invention relates to nonsteroidal anti-inflammatory compositions containing, as protectants against gastrointentinal injury caused by said nonsteroidal anti-inflammatory drug (hereinafter sometimes referred to as NSAID), a protectant selected from the group consisting of $H_1$ blockers, $H_2$ blockers, beta-adrenergic agonists, and combinations thereof. More particularly, it concerns compositions of this character, that also contain an alkalizing agent, and a process that uses such compositions. The terms $H_1$ blockers and $H_2$ blockers are used herein to refer to the histamine $H_1$- and $H_2$-receptor blockers, respectively.

$H_1$ blockers, $H_2$ blockers, as well as beta-adrenergic agonists, have been shown to offer some protection against gastrointestinal injury that is sometimes caused by the administration of NSAIDs. These, however, have suffered from some very distinct disadvantages. Among such advantages is the delay in relieving the subjective symptoms of gastric distress that is experienced by individuals who have taken such products.

It has now been found that the aforesaid disadvantages may be avoided by also incorporating an alkalizing agent in said NSAID composition containing a gastrointestinal protectant selected from the group consisting of $H_1$ blockers, $H_2$ blockers, beta-adrenergic agonists, and combinations thereof. In addition, it has been found that by incorporating said alkalizing agent in the compositons of interest there is often also observed an improvement in the ability of such compositions to protect against gastrointestinal injury that may be caused by said NSAIDs.

It has been suggested in the prior art that the coadministration of cimetidine with an antacid is to be avoided. In this connection, attention is directed to the "Physicians Desk Reference", 40th Edition, 1986, page 1726 and AMA Drug Evaluations" 5th Edition p. 1267. The latter is prepared and published by the American Medical Association, Chicago, Ill. In contrast to this, applicants did not observe any reduction in efficacy when the alkalizing agents were coadministered with $H_2$- or $H_1$-blockers and a NSAID.

It has also been reported in prior art that $H_2$-receptor blocking agents or antagonists protect against aspirin-induced lesions in certain laboratory animals. One such study is reported in Gastroenterology Vol. 88, NO. 5 part 2, p. 1344. This reference teaches nothing with regard to the use of an alkalizing agent as is characteristic of the present invention.

Cyproheptadine has been evaluated as a protectant against aspirin-induced gastric injury (Indian J. Med. Res. 1980, 71, p. 926-32). Although cyproheptadine may have some $H_1$-receptor antagonist properties, it does not act exclusively at the $H_1$-receptor sites but rather acts predominantly at serotonin-receptor sites (Goodman and Gilman "The Pharmacological Basis of Therapeutics", 7th Edition, p. 634). In addition, in the Indian Journal reference, the aspirin and cyproheptadine are not coadministered but are given serially. This is to be contrasted with the present invention in which the $H_2$- or $H_2$-receptor blocker or the beta-adrenergic agonist is coadministered with the aspirin. Furthermore, the treatment with cyproheptadine in accordance with the Indian reference is reported as not modifying the gastric acidity. This is also in contrast with the experience in this invention in which significant modification of gastric acidity takes place with the administration of aspirin and gastroprotectants utilized for the present purposes. Still a further distinction of the instant invention over the Indian Journal teaching is the fact that in the latter cyproheptadine was administered by intraperitoneal injection prior to the intragastric administration of the aspirin. This is to be contrasted with the fact that the compositions of the present invention lend themselves to oral administration at which time the NSAID and the $H_1$- or $H_2$-receptor blocker are coadministered. Most importantly perhaps, like the other reference discussed above, the Indian Journal reference nowhere suggests the use nor the advantages that follow from its use of an alkalizing agent. This, as will be made clear below, is an essential feature of the present invention.

The NSAIDs form a well-known class of drugs that are anti-inflammatory analgesics. These have the common property of inhibiting the formation of prostaglandins, which have a protective effect on the gastrointestinal mucosa (Goodman and Gilman "The Pharmacological Basis for Therapeutics" 7th Edition, p. 678). It is because of this inhibiting effect that the oral administration of drugs of this class may result in gastrointestinal injury and/or bleeding and is at least part of the problem that the present invention seeks to reduce or eliminate.

A number of NSAIDs are known in the prior art to which the present invention has application. The most commonly known group are the salicylates of which aspirin is the prime example. A further group of NSAIDs that have utility in connection with the instant invention are the proprionic acid derivatives. Included in this group are ibuprofen and naproxen. A further group of NSAIDs, employable herein, are the fenamates and compounds closely related to them structurally. These may be illustrated by such compounds as mefenamic acid, meclofenamate sodium, diclofenac and its sodium salt. Also belonging to the class NSAIDs with which the present invention is concerned are the indole derivatives (e.g. indomethacin); pyrrole alkanoic acid derivatives (e.g. tolmetin); pyrazalone derivatives (e.g. phenylbutazone); oxicams (e.g. piroxicam), etc.

The NSAID will be contained in the composition of this invention at concentrations at which it is generally found in therapeutic NSAID compositions intended for oral administration. This will usually be a pharmaceutically acceptable analgesic/anti-inflammatory dose.

A number of $H_1$- and $H_2$-receptor blockers are known in the prior art which are useful for the purposes of the present invention. By way of illustrating the $H_1$-receptor blockers that may be employed herein, mention may be made of the following: ethanolamines (e.g. diphenhydramine or its hydrochloride salt; carbinoxamine or its maleate salt); ethylenediamines (e.g. tripelennamine or its hydrochloride or nitrate salts); alkylamines (e.g. chlorpheniramine or its maleate salt, brompheniramine or its maleate salt); piperazines (e.g. hydroxyzine or its hydrochloride or pamoate salts, cyclizine or its hydrochloride or lactate salts, meclizine or its hydrochloride salts); etc. To exemplify the $H_2$-receptor blockers that may be advantageously used in the practice of this invention the following are given: cimetidine, ranitidine, famotidine, etc.

The $H_1$- and $H_2$-receptors blockers may be used in the form of their bases or in the form of their pharmaceutically acceptable salts. When employed as salts these will usually be acid addition salts wherein the acid portion may be hydrochloride, maleate, ascorbate, citrate, pamoate, lactate, tartrate, sulfate, etc.

The quantity of $H_1$-receptor blocker that will be contained in the composition of this invention may vary somewhat because of the variations in the anticholinergic activity that these agents exhibit. All that is required is that an effective amount be present so that the $H_1$-receptor blocker can make its contribution as a protectant against NSAID-induced gastrointestinal injury.

Similarly, the quantity of $H_2$-receptor blocker in the present composition may also vary. Again, all that is required is that amount employed be an effective protectant quantity which will enable the $H_2$-receptor blocker to play its part as a gastrointestinal protectant.

A number of beta-adrenergic agonists are known in the prior art which are useful for the purposes of this invention. Of special interest are isoproterenol which is a mixed beta-1 and beta-2 agonist and terbutaline which is a more selective beta-2 agonist. By way of illustrating other beta-adrenergic agonists that may be employed herein, the following are given: metaproterenol, albuterol, ritodrine. All of these may be employed as such or as pharmaceutically acceptable salts.

As with the other active ingredients contained in the compositions of this invention, the quantity of beta-adrenergic agonist that will be contained therein may also vary somewhat. Again, all that is required is that it be contained in said composition in an amount which will enable the beta-adrenergic agonist to play its part as a gastrointestinal protectant.

As indicated above, it is a feature of the present invention to incorporate in the instant composition an alkalizing agent. Since this composition is intended for oral administration, the akalizing agent employed will be one which is a pharmaceutically acceptable one that may be tolerated at the concentrations at which it is administered. A number of such alkalizing agents are known in this art which are suitable for the present purposes. By way of illustration, the following may be mentioned: sodium bicarbonate, magnesium carbonate, calcium carbonate, magnesium oxide, magnesium hydroxide, magnesium trisilicate, aluminum hydroxide, aluminum carbonate, potassium bicarbonate, etc.

The quantitive relationships of the various components of the composition of this invention may be expressed on the basis of the average daily dose of the ingredient contained in the product. This will take the form of weight of the ingredient per kg of body weight of the subject per day (e.g. milligrams or grams/kg of body weight/day). In general, this relationship may be expressed for the various ingredients as follows:

(a) NSAID: from about 10 mg/kg/day to about 100 mg/kg/day; preferred range from about 15 mg/kg/day to about 75 mg/kg/day.

(b) $H_2$-receptor blocker (when employed): from about 0.01 mg/kg/day to about 1 g/kg/day; preferred range from about 0.01 mg/kg/day to about 10 mg/kg/day.

(c) $H_1$-receptor blocker (when employed): from about 2.5 ug/kg/day to about 500 mg/kg/day; preferred range from about 0.1 mg/kg/day to about 50 mg/kg/day.

(d) beta-adrenergic agonist (when employed): from about 0.30 ug/kg/day to about 500 mg/kg/day; preferred range from about 0.01 mg/kg/day to about 10 mg/kg/day.

(e) alkalizing agent: from about 0.02 mEq/kg/day to about 10 mEq/kg/day; preferred range from about 0.04 mEq/kg/day to about 2 mEq/kg/day.

The compositions of the present invention may also be made up in unit dosage forms. Each unit dosage form will be sized and contain the ingredients in such amount that they may be taken orally in comfortable and convenient manner. Given below are the quantities of each type of active ingredient, when present in the composition, that will be contained in each:

TABLE I

| Ingredient | mg. per Unit dose General |
|---|---|
| NSAID | about 200 mg to about 600 mg. |
| $H_1$ Blocker | about 0.01 mg to about 70 mg. |
| $H_2$ Blocker | about 0.5 mg to about 350 mg |
| Beta-Adrenergic Agonist | about 0.7 mg to about 70 mg. |
| Alkalizing Agent | about 2 mEq to about 10 mEq |

The present products may be made into capsules, tablets, powders or caplets and may be film-coated, enteric-coated or formulated into sustained-release dosage forms or liquid dosage compositions. When formed into tablets or caplets they may contain adjuvants that facilitate the tableting of the product or enhance its elegance or dissolution rates. Generally illustrative of the adjuvants that may be contained in the various dosage forms encompassed in the present invention, the following may be mentioned: disintegrating agents, binders, lubricants, fillers, glidents, surfactants, flavoring agents, sweeteners, solvents, liquid carriers, suspending agents, preservatives, etc. More particularly, the adjuvants that may be contained in the various dosage forms over and above the active ingredients are as follows:

Caplet and Tablet: Cellulose, lactose, corn starch, stearic acid, water, gelatin, talc, sterotix, magnesium stearate, terra alba, sucrose, agar, pectin, Cab-O-Sil, acacia, etc.

Capsule: Spray-dried lactose, dimethylsiloxane, corn starch, water, magnesium stearate, sucrose, agar, pectin, Cab-O-Sil, etc.

Liquid Dosage Forms: Polyethylene glycol, sucrose, povidone, sodium citrate, citric acid, flavor, color, quinine, salicylic acid, water, peanut oil, olive oil, sesame oil, etc.

Sustained-release compositions may contain such things as glyceryl monostearate or glyceryl distearate.

In addition, these products may also contain other pharmaceutically active ingredients, such as deconqestants, analqesic adjuvants, antihistamines, expectorants, antitussives, diuretics, other analqesics, other anti-inflammatory aqents, other antipyretics, other antirheumatics, antioxidants, vasodilators, smooth muscle relaxants, skeletal muscle relaxants, bronchodilators, vitamins, trace minerals, amino acids, biological peptides, etc.

The compositions of this invention are useful in treating conditions and symptoms that are classically treated by the administration of NSAIDs. These include headache pain, pain and inflammation associated with arthritis and other systemic diseases, elevated body temperatures, etc. A variety of regimens may be employed in treating these conditions in accordance with the present invention. This will depend upon the particular unit dosage form that is used in the regimen. In the typical case one to two tablets will be taken every 4 to 6 hours, as needed.

The following examples are given to further illustrate the present invention. It is to be understood, however, that the invention is not limited thereto.

EXAMPLE 1

| Aspirin | 325 mg |
| Diphenhydramine hydrochloride | 16.67 mg |
| Sodium bicarbonate | 5 mEq |

EXAMPLE 2

| Aspirin | 325 mg |
| Ranitidine hydrochloride | 3.33 mg |
| Sodium bicarbonate | 5 mEq |

EXAMPLE 3

| Aspirin | 325 mg |
| Metaproterenol sulfate | 0.83 mg |
| Sodium bicarbonate | 5 mEq |

To test the effectiveness of the composition of this invention in protecting the stomach against NSAID-induced muscosal injury each protectant, in combination with an alkalizing agent, is administered orally with aspirin in capsules. For purposes of comparison, the protectant alone or the alkalizing agent alone is administered with the aspirin. A standard dose of 975 mg of aspirin is administered with varying doses of protectant and or alkalizing agent.

All test formulations are prepared on the day of the tests. The capsules are placed in the back of the dog's throat. A catheter, with funnel attached, is positioned in the dog's stomach and 50 ml of deionized water are administered.

Healthy adult beagle dogs of either sex are selected for testing. Dogs are housed individually in stainless steel cages with grid floors to allow excreta to pass through. Room temperature in the holding rooms and test laboratories is maintained between 65° F. and 85° F. and relative humidity between 30% and 80%. Room lights remain on from 6:00 AM to 4:00 PM.

Each dog is trained to stand in a stanchion with sling support and to accept a bit tied in its mouth. A gastroscope is then passed through the bit into the dog's stomach. This training requires ten days to two weeks in most dogs.

To determine whether a dog is suitable for test purposes, its stomach is examined for a normal mucosa, and its gastric responsiveness to aspirin is evaluated (as under Test Procedure). An acceptable gastric irritation score in the antrum must be 5 or greater (on a scale of 0-7) 2 hours after dosage.

Food is withheld from test dogs for 24 hours before the test and during the test and water is allowed ad lib. The dogs are moved into a holding area away from the kennel. Fasted dogs of either sex are examined gastroscopically to ensure that their stomachs have normal healthy mucosal linings. The dogs are dosed orally with test formulations, which are flushed into their stomachs with 50 ml of deionized water. They are then re-examined 2 hours later for gastric petechiae and signs of bleeding according to the following scale:

0 = uniform, pale to dark pink mucosa
1 = darker pink or blotchy mucosa
2 = petechiae and/or light-red streaks
3 = few small lesions
4 = many or connected small lesions (striations)
5 = few large lesions
6 = many large lesions
7 = massive hemorrhagic damage Severity of bleeding for each treatment and at each time is calculated as the mean gastric irritation score.

In addition to the endoscopic observation of the gastric mucosa of each dog, a qualitative description of gastric fluid is recorded and a pH measurement is made of the gastric fluid. All of these are done 2 hours after administration of the test product.

A base line is established by measuring the various parameters after the administration of 975 m9 of aspirin. The normal resting stomach has an irritation score of 0 and a pH of 5 to 5.5. Aspirin given alone, produced injury with scores of approximately 5.5 after 2 hours. The gastric pH at this time was about 3.1.

The results of these tests are summarized in Tables II, III and IV below. Table II summarizes the results obtained with an $H_1$ blocker and alkalizing agents; Table III the results obtained with $H_2$ blockers and an alkalizing agent; and Table IV the results obtained with beta-adrenergic agonists and alkalizing agents. These tables also include the data obtained with the protectant or alkalizing agent alone. With each of the test compositions set forth in these tables, 975 mg of aspirin was simultaneously administered. The aspirin was contained in the same capsule along with the other test ingredients.

In these tests the active ingredients were administered in the following forms:
diphenhydramine: [hydrochloride]
ranitidine: [hydrochloride]
cimetidine: [free base]
terbutaline: [sulfate]
albuterol: [free base]
isoproterenol: [hydrochloride]

TABLE II

Non-steroidal Anti-inflammatory Compositions Protected Against Gastrointestinal Injury
with Combinations of $H_1$ Blocker and Alkalizing Agents.
Data Summary

|  | 2-Hour Data | | |
| --- | --- | --- | --- |
|  | (N) | Irritation Score | pH |
| Control | 13 | 0 | 5.7 |
| Aspirin 975 mg | 8 | 5.5 | 3.3 |
| Diphenhydramine (12.5 mg) + Aspirin (975 mg) | 4 | 5.5 | 1.4 |
| Diphenhydramine (25.0 mg) + Aspirin (975 mg) | 4 | 5.75 | 2.1 |

TABLE II-continued

Non-steroidal Anti-inflammatory Compositions Protected Against Gastrointestinal Injury with Combinations of $H_1$ Blocker and Alkalizing Agents.
Data Summary

|  | 2-Hour Data | | |
|---|---|---|---|
|  | (N) | Irritation Score | pH |
| Diphenhydramine (50.0 mg) + Aspirin (975 mg) | 5 | 4.0 | 3.6 |
| Magnesium Oxide (12 mEq) + Aspirin (975 mg) | 12 | 3.50 | — |
| Sodium Bicarbonate (15 mEq) + Aspirin (975 mg) | 6 | 2.0 | 5.5 |
| Diphenhydramine (25 mg) + Magnesium Oxide (15 mEq) + Aspirin (975 mg) | 4 | 1.0 | 5.8 |
| Diphenhydramine (25 mg) + Sodium Bicarb. (15 mEq) + Aspirin (975 mg) | 4 | 1.25 | 6.0 |
| Diphenhydramine (12.5 mg) + Magnesium Oxide (15 mEq) + Aspirin (975 mg) | 4 | 3.00 | 2.7 |
| Diphenhydramine (12.5 mg) + Sodium Bicarb. (15 mEq) + Aspirin (975 mg) | 4 | 3.25 | 3.4 |
| Diphenhydramine (6.25 mg) + Magnesium Oxide (15 mEq) + Aspirin (975 mg) | 3 | 5.33 | 1.8 |

TABLE III

Non-steroidal Anti-inflammatory Composition Protected Against Gastrointestinal Injury with Combinations of Certain $H_2$ Blockers and Alkalizing Agents.
Data Summary

|  | 2-Hour Data | | |
|---|---|---|---|
|  | (N) | Irritation Score | pH |
| Control | 13 | 0 | 5.7 |
| Aspirin (975 mg) | 8 | 5.5 | 3.3 |
| Ranitidine (10 mg) + Aspirin (975 mg) | 6 | 3.50 | 5.3 |
| Ranitidine (20 mg) + Aspirin (975 mg) | 8 | 1.88 | 5.9 |
| Ranitidine (50 mg) + Aspirin (975 mg) | 6 | 0.67 | 6.1 |
| $NaHCO_3$ (12 mEq) + Aspirin (975 mg) | 11 | 4.1 | 3.8 |
| $NaHCO_3$ (15 mEq) + Aspirin (975 mg) | 6 | 2.0 | 5.5 |
| Ranitidine (10 mg) + $NaHCO_3$ (10 mEq) + Aspirin (975 mg) | 5 | 3.00 | 5.3 |
| Ranitidine (50 mg) + $NaHCO_3$ (10 mEq) + Aspirin (975 mg) | 5 | 0.60 | 6.7 |
| Cimetidine (50 mg) + Aspirin (975 mg) | 5 | 2.40 | 5.6 |
| Cimetidine (150 mg) + Aspirin (975 mg) | 6 | 0.33 | 6.0 |
| Cimetidine (50 mg) + $NaHCO_3$ (4.8 mEq) + Aspirin (975 mg) | 6 | 2.83 | 4.4 |
| Cimetidine (50 mg) + $NaHCO_3$ (9.6 mEq) + Aspirin (975 mg) | 6 | 2.83 | 3.9 |
| Cimetidine (50 mg) + $NaHCO_3$ (14.4 mEq) + Aspirin (975 mg) | 6 | 1.33 | 5.1 |
| Cimetidine (150 mg) + Sodium Bicarb. (15 mEq) + Aspirin (975 mg) | 6 | 0.67 | 7.2 |

Note:
At the highest dose tested, the alkalizing agent gave added protection against aspirin-induced injury and reduction in pH.

TABLE IV

Non-steroidal Anti-inflammatory Compositions Protected Against Gastrointestinal Injury with Combinations of Certain Beta Agonists and Alkalizing Agents.
Data Summary

|  | 2-Hour Data | | |
|---|---|---|---|
|  | (N) | Irritation Score | pH |
| Control | 13 | 0 | 5.7 |
| Aspirin (975 mg) | 8 | 5.5 | 3.3 |
| Terbutaline (1.25 mg) + Aspirin (975 mg) | 4 | 4.0 | 2.9 |
| Terbutaline (2.50 mg) + Aspirin (975 mg) | 4 | 2.0 | 3.8 |
| Terbutaline (5.00 mg) + Aspirin (975 mg) | 8 | 1.4 | 4.0 |
| Terbutaline (10.0 mg) + Aspirin (975 mg) | 5 | 1.2 | 4.6 |
| Albuterol (2.0 mg) + Aspiring (975 mg) | 4 | 2.8 | 2.7 |
| Albuterol (4.0 mg) + Aspiring (975 mg) | 4 | 1.5 | 4.8 |
| Albuterol (8.0 mg) + Aspiring (975 mg) | 4 | 1.0 | 5.4 |
| Isoproterenol (7.5 mg) + Aspirin (975 mg) | 9 | 3.9 | 3.5 |
| Isoproterenol (15.0 mg) + Aspirin (975 mg) | 9 | 2.7 | 3.8 |
| Isoproterenol (30.0 mg) + Aspirin (975 mg) | 10 | 1.3 | 5.0 |
| Sodium Bicarbonate (15 mEq) + Aspirin (975 mg) | 6 | 2.0 | 5.5 |
| Magnesium Oxide (12 mEq) + Aspirin (975 mg) | 12 | 3.5 |  |
| Terbutaline (5.0 mg) + Sodium Bicarbonate (15 mEq) + Aspirin (975 mg) | 4 | 1.0 | 5.8 |
| Terbutaline (5.0 mg) + Magnesium Oxide (15 mEq) + Aspirin (975 mg) | 4 | 2.0 | 6.3 |
| Terbutaline (1.25 mg) + Sodium Bicarbonate (15 mEq) + Aspirin (975 mg) | 4 | 3.2 | 2.0 |
| Albuterol (2.0 mg) + Sodium Bicarbonate (15 mEq) + Aspirin (975 mg) | 4 | 0.75 | 5.7 |
| Isoproterenol (30 mg) + Sodium Bicarbonate (15 mEq) + Aspirin (975 mg) | 5 | 1.2 | 7.4 |

Note:
The concomitant use of these drugs may permit the use of a lower dose of the beta agonist without compromising objective or subjective tolerance.

What is claimed is:

1. An aspirin-containing composition in unit dose form having reduced potential for causing gastrointestinal injury occasioned by the aspirin, the composition comprising from about 200 to about 975 mg aspirin, about 25 mg diphenhydramine and its pharmacologically acceptable salts, and about 15 mEq of an alkalizing agent selected from the group consisting of sodium bicarbonate and magnesium oxide.

2. The composition of claim 1 wherein the aspirin is present in an amount of from about 200 to about 600 mg.